United States Patent
Hou et al.

(10) Patent No.: US 11,828,733 B2
(45) Date of Patent: Nov. 28, 2023

(54) DEVICE FOR TESTING STRENGTH AND SEALING PERFORMANCE OF CEMENT SHEATH AFTER PERFORATION AND USING METHOD THEREOF

(71) Applicant: Southwest Petroleum University, Sichuan (CN)

(72) Inventors: Duo Hou, Sichuan (CN); Zhongling Xiao, Sichuan (CN); Zhi Zhang, Sichuan (CN); Jian Ding, Sichuan (CN); Jiawei Wang, Sichuan (CN); Taihe Shi, Sichuan (CN)

( * ) Notice: Subject to any disclaimer, the term of this patent is extended or adjusted under 35 U.S.C. 154(b) by 0 days.

(21) Appl. No.: 17/690,018

(22) Filed: Mar. 9, 2022

(65) Prior Publication Data
US 2023/0168164 A1 Jun. 1, 2023

(30) Foreign Application Priority Data
Nov. 26, 2021 (CN) .......................... 202111423502.1

(51) Int. Cl.
 *G01N 3/02* (2006.01)
 *G01M 3/00* (2006.01)
 (Continued)

(52) U.S. Cl.
 CPC .............. *G01N 3/02* (2013.01); *G01M 3/002* (2013.01); *G01M 3/26* (2013.01); *G01N 33/383* (2013.01); *E21B 43/116* (2013.01); *E21B 47/005* (2020.05)

(58) Field of Classification Search
CPC .... G01N 33/383; E21B 43/116; E21B 47/005
See application file for complete search history.

(56) References Cited

U.S. PATENT DOCUMENTS

2017/0205388 A1* 7/2017 Thomas ................. E21B 47/005
2020/0165896 A1* 5/2020 Skeels ..................... E21B 41/00

FOREIGN PATENT DOCUMENTS

CN       1072990 A  *  6/1993
CN     104153760 A  * 11/2014
(Continued)

OTHER PUBLICATIONS

CN-106483045-A—translate (Year: 2017).*
(Continued)

*Primary Examiner* — Kristina M Deherrera
*Assistant Examiner* — Fatemeh Esfandiari Nia

(57) ABSTRACT

The invention discloses a device for testing strength and sealing performance of cement sheath after perforation, comprising a cement sheath curing maintenance simulation component, a perforation operation simulation component, and a cement sheath performance test component. By simulating the detonation effect and fluid-solid coupling effect, quantitatively testing the internal transverse crack and longitudinal crack propagation size, compressive strength and tensile strength, permeability, blowby pressure, blowby velocity and other parameters of the cement sheath, drawing the relation curve between different perforation distances and the maximum blowby pressure and permeability of the cement sheath, determining the perforation distance $H_p$ where the blowby of the cement sheath does not occur, determining the perforation distance $H_K$ to ensure the sealing of the cement sheath, and using min ($H_p$, $H_K$), the critical perforation distance that the cement sheath has sufficient strength to prevent blowby and meet the sealing requirements can be determined.

10 Claims, 3 Drawing Sheets

(51) Int. Cl.
*G01M 3/26* (2006.01)
*G01N 33/38* (2006.01)
*E21B 47/005* (2012.01)
*E21B 43/116* (2006.01)

(56) References Cited

FOREIGN PATENT DOCUMENTS

| CN | 106483045 A | * | 3/2017 |
| CN | 111307690 A | * | 6/2020 |
| CN | 113482581 A | * | 10/2021 |

OTHER PUBLICATIONS

CN-113482581-A—translate (Year: 2021).*
CN-1072990-A—translate (Year: 1993).*
CN-111307690-A—translate (Year: 2020).*
CN-104153760-A—translate (Year: 2014).*

* cited by examiner

DEVICE FOR TESTING STRENGTH AND SEALING PERFORMANCE OF CEMENT SHEATH AFTER PERFORATION AND USING METHOD THEREOF

BACKGROUND OF THE INVENTION

1. Field of the Invention

The invention relates to the technical field of mining exploitation, in particular to a device for testing strength and sealing performance of cement sheath after perforation, and also relates to an evaluation method for using the device to simulate and test the strength performance, internal crack size, and sealing performance of the cement sheath after perforation.

2. Description of the Related Art

Perforation well completion is the most extensive and practical well completion method, that is, after drilling through the oil and gas layer, running the casing of the oil layer to the bottom of the oil layer, injecting cement into the annular space of the oil layer and the wellbore to form a cement sheath, running the incident hole gun, and detonating the perforating bomb to explode to generate high-speed energy flow, penetrating the oil layer casing and cement sheath in turn and penetrating into the oil layer to a certain depth to establish a channel for oil and gas flow into the wellbore. Reasonable perforating operation parameters are conducive to protecting oil and gas layers, ensuring the implementation of production stimulation measures such as layered extraction, water injection, acid fracturing, and so on. At the same time, it is of great significance to increase productivity, improve oil and gas field development benefits, and reduce workover operations. However, the cement sheath is a brittle material, and its essence is a porous structure system with a continuous phase distribution of framework and pores. When impacted by the perforation detonation energy flow, the internal cracks in the cement sheath nucleate and expand rapidly, as a result, the cement sheath body loses its sealing ability, the cementing I interface between the cement sheath and the casing has micro-annular gaps, and the cementing II interface between the cement sheath and the rock fails. The loss of the wellbore of the perforated section of sealing will seriously affect the safety of deep and ultra-deep wells, and at the same time may cause a series of wellbore integrity risk accidents.

The current method to solve the above problems is mainly to develop a high-performance cement slurry system and optimize the perforation operation parameters, but it is impossible to truly grasp the influence of different perforation operation parameters on the performance of the cement sheath; only through the simulation test of the change rule of the strength performance of the cement sheath after perforation, it provides the strength mechanical parameters for the optimization design of the cement slurry system additives; after simulating and testing the sealing capacity of the cement sheath after perforation, it provides a basis for sealing integrity for the adjustment of perforation parameters; thereby, it can effectively guide the coordination and matching of the comprehensive performance of the cement slurry system after curing with the perforation operation parameters. Therefore, the test of the strength and sealing performance of the cement sheath after perforation has extremely important value in theory and engineering.

In view of the sealing performance of the cement sheath after perforation, numerical simulation methods are mostly used for calculation and prediction, while physical simulation methods often adopt two methods: prefabricated perforation and detonation to form perforations according to the perforating operation parameters.

The method of prefabricated perforation, that is, the casing-cement sheath does not experience perforation detonation, and the method of directly processing the prefabricated perforation, such as the method of prefabricating perforation holes in the casing wall of the patent CN113107467A, simulates the sealing performance test of the casing-cement sheath-stratum combination after perforation; the aperture, hole density, phase and other parameters of the prefabricated perforations are consistent with the perforation operation parameters; fluid simulation is used to test the sealing performance of the cement sheath and cementing interface. The patent of CN108982225A adopts physical simulation of the non-uniformly distributed load in the horizontal and vertical directions of the stratum; according to the perforation parameters, opening round holes in the corresponding parts of the casing-cement sheath, measuring and analyzing the strain of the casing-cement sheath, and providing experimental basis for the analysis of the failure mechanism of the casing-cement sheath after perforation. The patent of CN106483045A adopts physical simulation of casing internal pressure, through setting simulation perforation channel in casing-cement sheath-stratum surrounding rock, and installing flowmeter on the end face to measure the flow of oil, gas or water, determining the interlayer isolation ability after the cement sheath is perforated.

The physical simulation method of perforating operation, that is, the method of perforating perforations formed by the detonation energy flow impacting the casing-cement sheath with parameters such as perforating bullet, charge amount, aperture, phase, and penetration depth consistent with the perforating operation, such as the method of the patent CN113482581A, adopts double-layer casing, solidified cement sheath in the middle, and wrapped concrete target on the outside, and specifically tests whether the perforation diameter and maximum penetration depth meet the perforation process, puts forward a critical criterion for the penetration of double-layer casing, and provides experimental data support for the optimization of perforating guns and perforating bullets under high temperature and high pressure working conditions; such experiments involve complex perforation parameters, high risk of perforation explosion, strict safety qualification requirements, lack of risk-controllable, safe and reliable physical simulation methods, and it is impossible to quantitatively evaluate the comprehensive influence of different perforation parameters on the casing-cement sheath-formation combination of deep and ultra-deep wells, which seriously affect the performance optimization of deep and ultra-deep well cement slurry system and the optimization and adjustment of perforation process parameters, and hinder the development of wellbore integrity control technology for perforation operations.

In summary, conventional wellbore seal integrity evaluation methods have the following shortcomings:

(A) The perforation holes on the casing-cement sheath-stratum combination are formed by the impact of non-detonation energy flow, and the test results of the sealing ability of the physical simulation cement stratum cannot be applied to the field perforation operating conditions.

(B) The cement sheath is a brittle material with a porous structure with a framework-pore continuous phase distribution, which is very easy to crack when it is impacted by the perforation detonation energy flow, and its internal crack nucleation and propagation characteristics cannot be tested.

(C) The perforation and its surrounding casing-cement sheath-stratum combination changes after perforation, which is quite different from the mechanical properties of the cement sheath after curing maintenance, so it is impossible to test the mechanical properties of the cement sheath after perforation.

SUMMARY OF THE INVENTION

Based on this, it is necessary to provide a device for testing strength and sealing performance of cement sheath after perforation and a using method thereof in response to the technical problems in the above prior art.

The embodiment of the invention provides a device for testing strength and sealing performance of cement sheath after perforation, comprising a cement sheath curing maintenance simulation component, a perforation operation simulation component, and a cement sheath performance test component;

wherein the cement sheath curing maintenance simulation component comprises:
a casing;
stratum rocks, which are arranged outside the casing, and the casing and the stratum rocks enclose a closed annular space; a cement sheath is in curing maintenance in the closed annular space;
the perforation operation simulation component comprises:
a perforation gun, and a gun body thereof is provided inside the casing; the gun body is provided with a plurality of perforation bullets; the plurality of perforation bullets are connected in series via a detonating cord and pass through the top of the casing;
a kill fluid, which is tanked between the casing and the gun body;
the cement sheath performance test component comprises:
a channeling verification booster pump; the channeling verification pressure is applied to the lower end surface of the cement sheath through a channeling verification pipeline and a gas-permeable cement isolation ring;
a channeling verification pressure sensor, which is provided on the channeling verification pipeline;
a temperature and pressure control system, which is electrically connected to the channeling verification pressure sensor, and is used to draw the blowby pressure curve under perforation parameters and perforation distance to test the strength and sealing performance of the cement sheath after perforation.

Further, a casing sealing ring and a lower plug are sequentially provided between the casing and the bottom of the stratum rocks from the inside to the outside; an upper sealing head and an upper plug are sequentially provided between the casing and the top of the stratum rocks from the inside to the outside.

Further, the cement sheath curing maintenance simulation component further comprises:
a casing booster pump, which is communicated with the casing through a casing pressure pipeline;
a casing internal pressure control valve, which is provided on the casing pressure pipeline close to the casing booster pump.

Further, the cement sheath curing maintenance simulation component further comprises:
a casing heating device, which is provided in the casing;
a casing temperature and pressure sensor, which is provided in the casing and is electrically connected to the temperature and pressure control system.

Further, the cement sheath curing maintenance simulation component further comprises:
a rubber cylinder, which is surrounded outside the stratum rocks;
a hydraulic chamber, which is surrounded outside the rubber cylinder;
a hydraulic cylinder, which is surrounded outside the hydraulic chamber;
a stratum heating jacket, which is surrounded outside the hydraulic cylinder;
a confining pressure booster pump, which is communicated with the top of the hydraulic chamber through a confining pressure booster pipeline;
a confining pressure sensor, which is provided on the confining pressure booster pipeline and is electrically connected to the temperature and pressure control system;
a confining pressure relief valve, which is connected to the bottom of the hydraulic chamber through a confining pressure relief pipeline.

Further, the perforation gun comprises:
a gun body;
a gun head, which is provided at the top of the gun body and is located in the casing;
a gun tail, which is provided at the bottom of the gun body and is located in the casing;
a gun body upper plug, which is provided outside the casing and located directly above the gun body, and is used to guide the detonating cord;
a gun body lower plug, which is provided at the bottom of the gun tail and located in the casing;
a gun body handle, which is provided at the top of the gun body upper plug.

Further, the perforation operation simulation component comprises:
an inner iron sleeve, which is surrounded outside the stratum rocks;
an outer iron sleeve, which is surrounded outside the inner iron sleeve, and concrete is cured between the space enclosed by the inner iron sleeve and the outer iron sleeve.

A using method of the device for testing strength and sealing performance of cement sheath after perforation, comprising:
according to the curing maintenance parameters, a cement sheath is in curing maintenance in the closed annular space enclosed by the casing and the stratum rocks;
according to the perforation operation parameters, perforating with a perforation gun and a detonator equipped with perforation bullets and a detonating cord;
connecting the channeling verification pressure sensor and the channeling verification booster pump to the channeling verification pipeline, selecting an initial pressure $P_0$ to start the channeling verification, and observing the channeling verification curve of the temperature and pressure control system; if the temperature and pressure within 30 minutes are within the range of $P_0 \times (1 \pm 10\%)$, then selecting the next pressure $P_1$, $P_2$, $P_3$ . . . for channeling verification; monitoring and drawing the relation curve between the blowby pressure curve and time, increasing the pressure until the blowby of the cement sheath occurs, recording the maximum pressure before the blowby occurs as $P_{C0}$, and calculating the blowby velocity $v_0$;

taking out the cement sheath, measuring the propagation direction of the crack and the size of the crack at different positions from the perforation hole, and drawing the relation curve between the distance of the perforation hole and the crack size;

processing the cement stone tensile specimens, compressive specimens and permeability test specimens at different positions away from the perforation hole; testing the compressive strength, tensile strength $\sigma_{t0}$ and permeability $K_0$ of the cement stone after perforation, and drawing the relation curve between the perforation distance and the tensile strength $\sigma_{t0}$, compressive strength $\sigma_{R0}$ and permeability $K_0$;

selecting the next perforation distance $H_1$, $H_1 < H_0$, and measuring the maximum pressure $P_{C1}$ under this perforation distance and the blowby velocity $v_1$, until the designed perforation distances $H_2, H_3 \ldots$ are all tested;

drawing the pressure blowby curve at different perforation distances; drawing the relation curves between different perforation distances $H_0, H_1, H_2, H_3 \ldots$ and the maximum blowby pressure $P_{C0}, P_{C1}, P_{C2}, P_{C3} \ldots$, permeability $K_0, K_1, K_2, K_3 \ldots$;

according to the target stratum pressure $P_p$, determining the critical blowby pressure $P_C$ of the cement sheath; when setting the target stratum pressure $P_p$, ensuring that the perforation distance that the blowby of the cement sheath does not occur is greater than or equal to $H_p$;

determining the critical permeability $K_C$ of the cement sheath according to the annulus pressure $P_A$ control requirements; under the setting of the annulus pressure $P_A$ control requirements, ensuring that the perforation distance of the cement sheath sealing is greater than or equal to $H_K$;

selecting the minimum perforation distance ($H_p$, $H_K$) as the critical perforation distance to ensure the strength and sealing performance of the cement sheath.

The curing maintenance parameters comprise:

according to the cementing and perforation operating conditions of the target well, determining the cement slurry system, casing temperature, internal pressure, stratum temperature, confining pressure, temperature and pressure changes during cementing, and waiting on cement setting time during the cementing operation.

The perforation operation parameters comprise: aperture, phase, hole density, penetration depth, and explosive payload during the perforation operation.

Compared with the prior art, the device for testing strength and sealing performance of cement sheath after perforation provided by an embodiment of the invention has the following advantageous effects:

In order to solve the requirement that the conventional cement sheath sealing performance evaluation method after perforation is not suitable for the indoor evaluation of perforation completion conditions, the invention proposes a device for testing strength and sealing performance of cement sheath after perforation. The invention simulates the detonation effect of the perforation operation, and the detonation high-speed energy flow impacts the casing-cement sheath-stratum combination and forms the perforation holes, simulates the damage effect of the perforation operation on the combination, tests the sealing ability of the cement sheath, the size of internal cracks and its strength performance, draws the relation curve between the cement sheath blowby pressure, permeability and perforation distance, and also provides experimental methods and data support for the optimization design of cement slurry system and perforation parameters.

Figure 1:
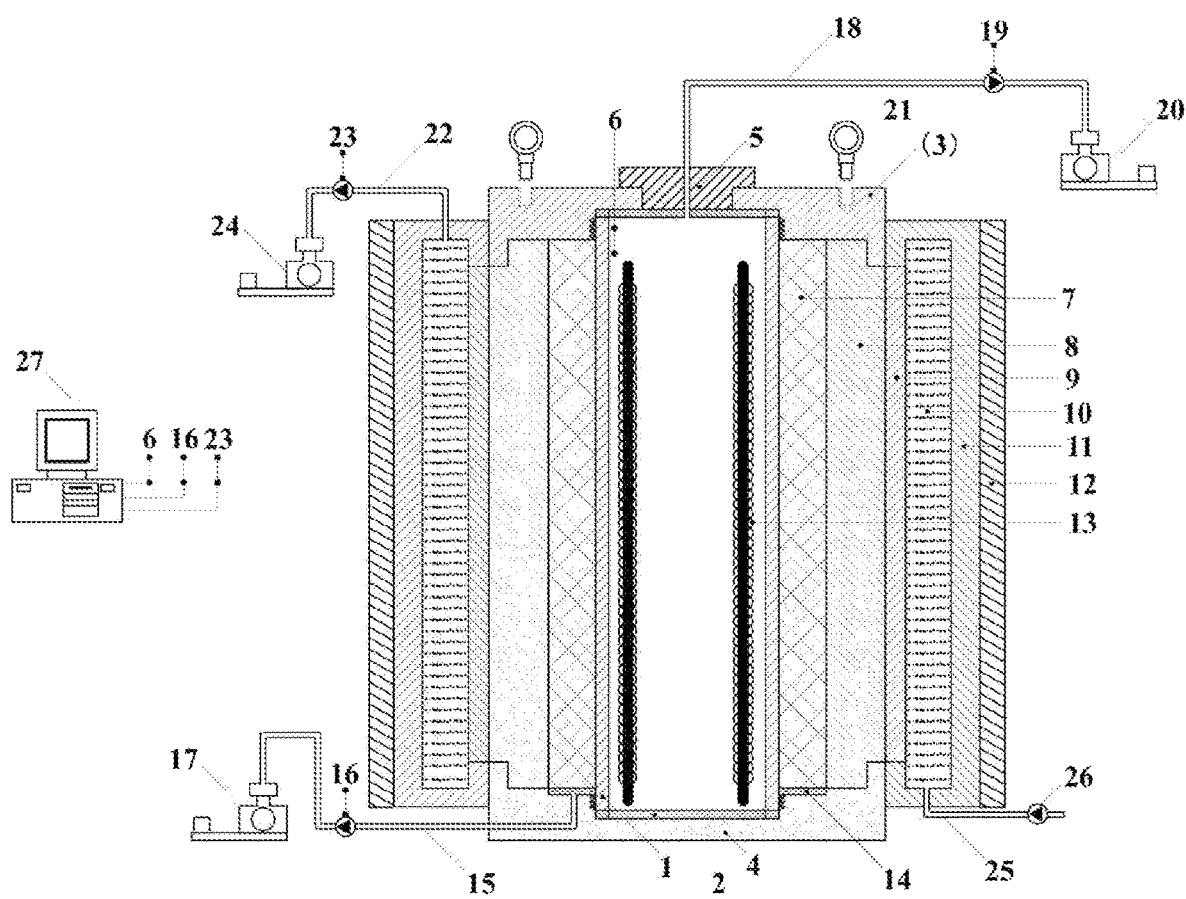
FIG. 1 is a schematic diagram of the structure of the device for testing strength and sealing performance of cement sheath after perforation provided by an embodiment of the invention.

DESCRIPTION OF REFERENCE SIGNS 1 refers to the casing; 2 refers to the casing sealing ring; 3 refers to the upper plug; 4 refers to the lower plug; 5 refers to the upper sealing head; 6 refers to the casing temperature and pressure sensor; 7 refers to the cement sheath; 8 refers to the stratum rocks; 9 refers to the rubber cylinder; 10 refers to the hydraulic chamber; 11 refers to the hydraulic cylinder; 12 refers to the stratum heating jacket; 13 refers to the casing heating device; 14 refers to the gas-permeable cement isolation ring; 15 refers to the channeling verification pipeline; 16 refers to the channeling verification pressure sensor; 17 refers to the channeling verification booster pump; 18 refers to the casing pressure pipeline; 19 refers to the casing internal pressure control valve; 20 refers to the casing booster pump; 21 refers to the channeling verification device lifting ring; 22 refers to the confining pressure booster pipeline; 23 refers to the confining pressure sensor; 24 refers to the confining pressure booster pump; 25 refers to the confining pressure relief pipeline; 26 refers to the confining pressure relief valve; 27 refers to the temperature and pressure control system; 28 refers to the gun head; 29 refers to the gun body; 30 refers to the perforation bullets; 31 refers to the detonation cord; 32 refers to the gun tail; 33 refers to the gun body upper plug; 34 refers to the gun body lower plug; 35 refers to the gun body handle; 36 refers to the kill fluid; 37 refers to the inner iron sleeve; 38 refers to the concrete; 39 refers to the outer iron sleeve.

DETAILED DESCRIPTION OF THE PREFERRED EMBODIMENTS

In order to make the purpose, technical solutions, and advantages of the invention clearer, the invention will be further described in detail hereinafter with reference to the drawings and embodiments. It should be understood that the specific embodiments described herein are only used to explain the invention, and not used to limit the invention.

One embodiment of the invention discloses a device for testing strength and sealing performance of cement sheath after perforation, wherein the device specifically comprises:

a cement sheath curing maintenance simulation component, a perforation operation simulation component, and a cement sheath performance test component. The invention can simulate the cyclic and alternating conditions of casing temperature, casing internal pressure, stratum temperature, and stratum confining pressure during cementing operations, to realize the solidification and maintenance of the cement sheath, and can simulate parameters such as aperture, phase, hole density, penetration depth, explosive payload, and other parameters during the perforation operation to realize the impact of detonation energy flow on the casing-cement sheath-stratum and complete the perforation. The invention provides a reliable experimental device and data support for cement slurry system design and perforation parameter optimization by quantitatively evaluating the size, strength and sealing performance of the internal cracks of the cement sheath under different perforation parameters.

With reference to FIG. 1, specifically, the cement sheath curing maintenance simulation component comprises: a casing 1, a casing sealing ring 2, an upper plug 3, a lower plug 4, an upper sealing head 5, a casing temperature and pressure sensor 6, a cement sheath, stratum rocks 8, a rubber cylinder 9, a hydraulic chamber 10, a hydraulic cylinder 11, a stratum heating jacket 12, a casing heating device 13, a casing pressure pipeline 18, a casing internal pressure control valve 19, a casing booster pump 20, a confining pressure booster pipeline 22, a confining pressure sensor 23, a confining pressure booster pump 24, a confining pressure relief pipeline 25, a confining pressure relief valve 26, and a temperature and pressure control system 27, which can simulate the cyclic and alternating conditions of casing temperature, casing internal pressure, stratum temperature, and stratum confining pressure during cementing operations, to realize the solidification and maintenance of the cement sheath.

Further, cement sheath curing maintenance simulation component encloses a closed annular space by the casing 1, the casing sealing ring 2, the upper plug 3, the lower plug 4, and the stratum rocks 8; the casing 1 is connected to the upper plug 3 and the lower plug 4 by threaded connection; the upper sealing head 5 and the casing sealing ring 2 are used for sealing; the inside of the casing 1 is provided with a casing heating device 13, which can heat the casing and simulate the casing temperature of the target wellbore.

Further, the upper plug 3 is provided with an upper sealing head 5 and a casing pressure pipeline 18, which is connected to a casing internal pressure control valve 19 and a casing booster pump 20, which can pressurize the inside of the casing and simulate the internal pressure of the target wellbore.

Further, the inside of the casing 1 is provided with a casing temperature and pressure sensor 6, which can monitor and record the temperature and pressure in real time; the outside of the stratum rocks 8 is provided with a stratum heating jacket 12; the rubber cylinder 9, the hydraulic chamber 10, the hydraulic cylinder 11, the confining pressure booster pipeline 22, the confining pressure sensor 23, the confining pressure booster pump 24, the confining pressure relief pipeline 25, the confining pressure relief valve 26 can heat and pressurize the stratum rocks 8 to simulate the stratum temperature and pressure near the target wellbore.

Further, the cement slurry system to be evaluated is tanked in a closed annular space, and the temperature and pressure control system 27 is used to control the temperature and pressure of the casing and the stratum respectively, which can simulate the cyclic alternating conditions of casing temperature, casing internal pressure, stratum temperature, and stratum confining pressure during the cementing operation, and wait until the cement sheath 7 is cured and maintained.

Further, the casing cement sheath stratum assembly preparation components comprise: a casing 2, a cement sheath 3, stratum rocks 4, a copper sleeve 5, a core plug 6, a casing core plug sealing component 7, a copper sleeve fixing flange 8, an assembly tightening flange 9, a pulling rod 10, a copper sleeve core plug sealing component 11, a tightening flange core plug sealing component 12, a tightening flange sealing flange 13, a tightening flange sealing flange bolt 14, and an assembly tightening flange pulling rod 15, which can realize the curing maintenance and preparation of the canned cement slurry system and the casing cement sheath stratum assembly.

Figure 2:
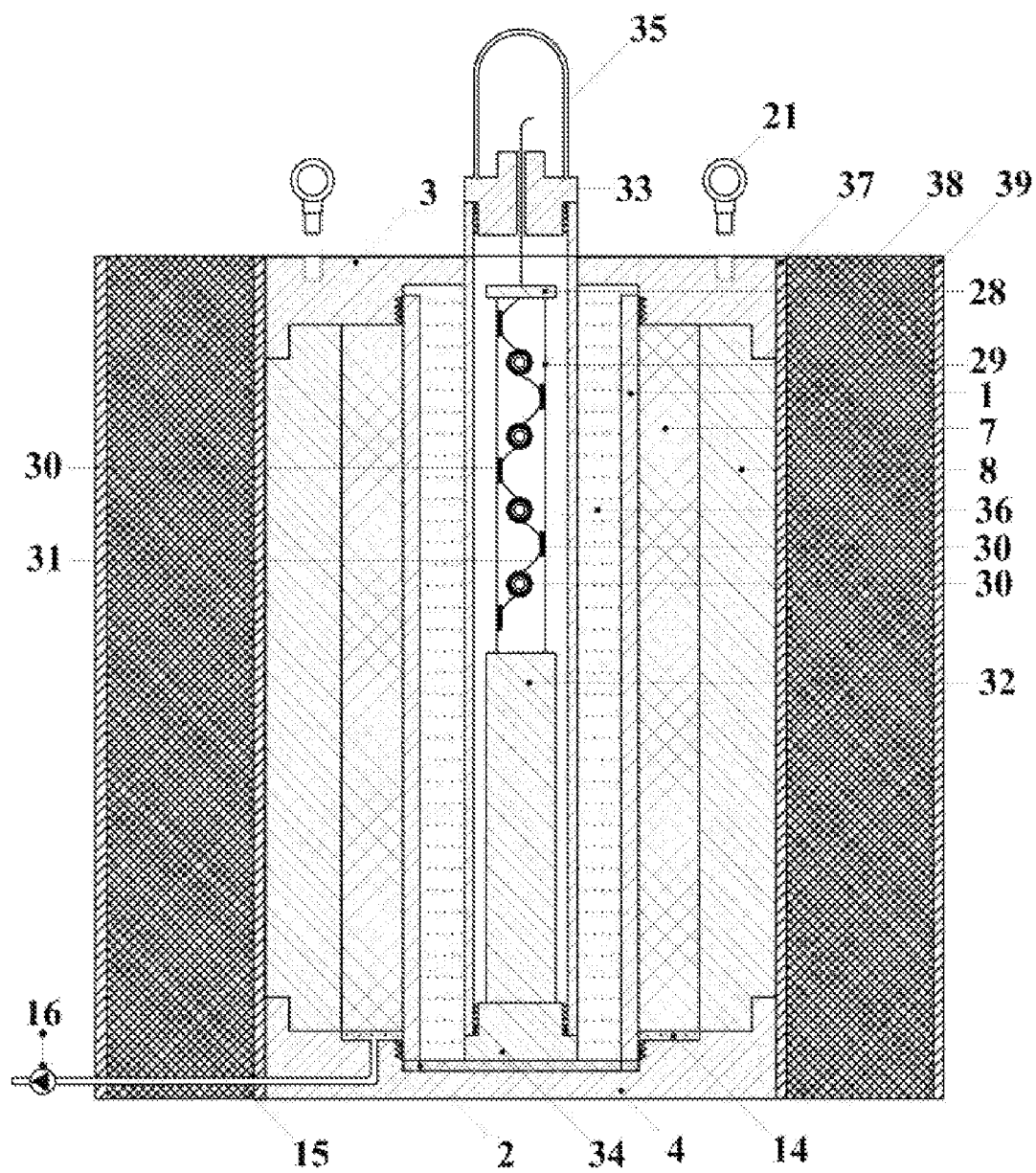
FIG. 2 is a schematic diagram of the structure of the perforation device.
Figure 3:
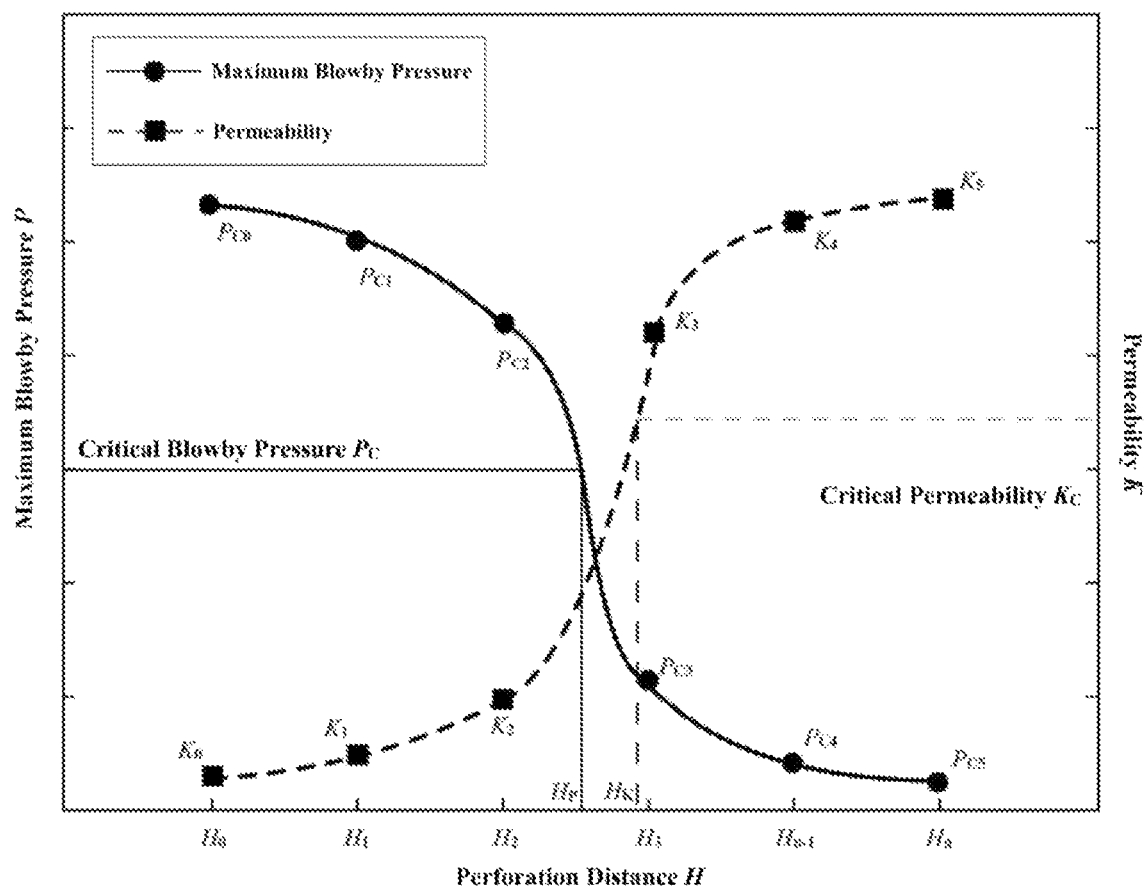
FIG. 3 is a test curve and a method for determining the critical perforation distance provided by an embodiment of the invention.

With reference to FIG. 2, specifically, the perforation operation simulation component comprises: a gun head 28, a gun body 29, perforation bullets 30, a detonation cord 31, a gun tail 32, a gun body upper plug 33, a gun body lower plug 34, a gun body handle 35, a kill fluid 36, an inner iron sleeve 37, and concrete 38, which can simulate parameters such as aperture, phase, hole density, penetration depth, explosive payload, and other parameters during the perforation operation to realize the impact of detonation energy flow on the casing-cement sheath-stratum and complete the perforation.

That is, the perforation operation simulation component is composed of a gun head 28, a gun body 29, a gun tail 32, a gun body upper plug 33, a gun body lower plug 34, and a gun body handle 35; the gun body 29 is provided with perforation bullets 30, and the explosive payload, arrangement phase, aperture, hole density, and penetration depth are consistent with the perforation parameters of the target wellborn. The detonating cord 31 connects all the perforating bullets in series and passes through the gun body upper plug 33. A kill fluid 36 is tanked between the casing 1 and the gun body 29. A certain thickness of concrete 38 is cured between the inner iron sleeve 37 and the outer iron sleeve 39 to simulate the damage of the cement sheath 7 caused by the fluid-solid coupling effect under the detonation effect of perforation operation.

Specifically, the cement sheath performance test component comprises: a gas-permeable cement isolation ring 14, a channeling verification pipeline 15, a channeling verification pressure sensor 16, a channeling verification booster pump 17, and a channeling verification device lifting ring 21, which can quantitatively evaluate the internal crack size, strength and sealing performance of the cement sheath under different perforation parameters, and provide data support for cement slurry system design and perforation parameter optimization.

That is, the cement sheath performance test component applies the channeling pressure by the channeling verification booster pump 17 to the lower end surface of the cement sheath 7 through the channeling verification pipeline 15 and the gas-permeable cement isolation ring 14. Through the channeling verification pressure sensor 16, the change of the blowby pressure can be monitored in real time, and the blowby pressure curve under the perforation parameters and perforation distance can be drawn.

One embodiment discloses a using method of the device for testing strength and sealing performance of cement sheath after perforation, wherein the method comprises:

according to the cementing and perforation operating conditions of the target well, determining the cement slurry system, casing temperature, internal pressure, stratum temperature, confining pressure, temperature and pressure changes during cementing, waiting on cement setting time, and other curing parameters during the cementing operation; determining the parameters such as aperture, phase, hole density, penetration depth, explosive payload and so on during perforation operation.

S2: placing the lower plug 4 steadily, applying sealing grease and connecting the casing 1 and the lower plug 4 through the threaded connection through the casing sealing ring 2; according to the installation and positioning of the steps set by the stratum rocks 8 and the lower plug 4, installing the rubber cylinder 9, the hydraulic cavity 10, the hydraulic cylinder 11, the stratum heating jacket 12, the gas-permeable cement isolation ring 14, the confining pressure booster pipeline 22, the confining pressure sensor 23, the confining pressure booster pump 24, the confining pressure relief pipeline 25, and the confining pressure relief valve 26 in sequence; installing the casing temperature and pressure sensor 6 and the casing heating device 13 inside the casing.

S3: preparing the cement slurry system and slowly and steadily pouring into the annular space between the casing 1 and the stratum rocks 8 along the casing wall, and installing the upper plug 3 using the channeling verification device lifting ring 21, then installing the upper sealing head 5, the casing pressure pipeline 18, the casing internal pressure control valve 19, and the casing booster pump 20 in sequence.

S4: connecting the temperature and pressure control system 27 to the casing temperature and pressure sensor 6 and the confining pressure sensor 23 in sequence; when the casing internal pressure and temperature and the stratum confining pressure and temperature reach the cementing operating conditions, the temperature and pressure control system 27 starts to monitor and record the temperature and pressure curve of the cement sheath 7 curing maintenance; the temperature and pressure control system 27 can be used to set the temperature and pressure alternation amplitude and alternation time to simulate the characteristics of wellbore conditions during cementing operations.

S5: after the cement sheath 7 is cured and maintained, removing the upper sealing head 5, the casing pressure pipeline 18, the casing internal pressure control valve 19, the casing booster pump 20, the rubber cylinder 9, the hydraulic chamber 10, the hydraulic cylinder 11, and the stratum heating jacket 12, etc.; according to the aperture, phase, hole density, penetration depth, and explosive payload, processing and manufacturing the perforating gun, and installing the perforating bullets 30 in the gun body 29; preliminarily determining a larger perforation distance $H_0$ that can guarantee the sealing performance of the cement sheath, then the height of the gun tail 32 is $H_0$; installing the gun head 28, the gun body upper plug 33, the gun body lower plug 34, and the gun body handle 35 in sequence; using the detonating cord 31 to connect all perforating bullets in series and pass through the upper plug 33, and injecting the kill fluid 36 into the annular space between the gun body 29 and the casing 1.

S6: a certain thickness of concrete 38 is cured between the inner iron sleeve 37 and the outer iron sleeve 39 to prevent the stratum rocks 8 from crushing damage.

S7: connecting the detonating cord 31 to the detonator, determining a sufficient safety distance, and detonating the perforating bomb on the premise of confirming safety to complete the perforation simulation operation.

S8: connecting the channeling verification pressure sensor 16 and the channeling verification booster pump 17 to the channeling verification pipeline 15, selecting an initial pressure $P_0$ to start the channeling verification, and observing the channeling verification curve of the temperature and pressure control system 27; if the temperature and pressure within 30 minutes are within the range of $P_0 \times (1 \pm 10\%)$, then selecting the next pressure $P_1$, $P_2$, $P_3$ . . . for channeling verification; monitoring and drawing the relation curve between the blowby pressure curve and time, increasing the pressure until the blowby of the cement sheath 7 occurs, recording the maximum pressure before the blowby occurs as $P_{C0}$, and calculating the blowby velocity $v_0$.

S9: taking out the cement sheath, measuring the propagation direction of the crack and the size of the crack at different positions from the perforation hole, and drawing the relation curve between the distance of the perforation hole and the crack size.

S10: processing the cement stone tensile specimens, compressive specimens and permeability test specimens at different positions away from the perforation hole; testing the compressive strength, tensile strength $\sigma_{t0}$ to and permeability $K_0$ of the cement stone after perforation, and drawing the relation curve between the perforation distance and the tensile strength $\sigma_{t0}$, compressive strength $\sigma_{R0}$ and permeability $K_0$.

S11: selecting the next perforation distance $H_1$, $H_1 < H_0$, and measuring the maximum pressure $P_{C1}$ under this perforation distance and the blowby velocity $v_1$, until the designed perforation distances $H_2$, $H_3$ . . . are all tested.

S12: drawing the pressure blowby curve at different perforation distances; drawing the relation curves between different perforation distances $H_0$, $H_1$, $H_2$, $H_3$ . . . and the maximum blowby pressure $P_{C0}$, $P_{C1}$, $P_{C2}$, $P_{C3}$ . . . , permeability $K_0$, $K_1$, $K_2$, $K_3$ . . . .

S13: according to the target stratum pressure $P_p$, determining the critical blowby pressure $P_C$ of the cement sheath; when setting the target stratum pressure $P_p$, ensuring that the perforation distance that the blowby of the cement sheath does not occur is greater than or equal to $H_p$.

S14: determining the critical permeability $K_C$ of the cement sheath according to the annulus pressure $P_A$ control requirements; under the setting of the annulus pressure $P_A$ control requirements, ensuring that the perforation distance of the cement sheath sealing is greater than or equal to $H_K$.

S15: selecting the minimum perforation distance ($H_p$, $H_K$) as the critical perforation distance to ensure the strength and sealing performance of the cement sheath.

In summary, by simulating the detonation effect and fluid-solid coupling effect on the casing-cement sheath-stratum under perforating operation parameters, quantitatively testing the internal transverse crack and longitudinal crack propagation size, compressive strength and tensile strength, permeability, blowby pressure, blowby velocity and other parameters of the cement sheath, drawing the relation curve between different perforation distances and the maximum blowby pressure and permeability of the cement sheath, determining the perforation distance $H_p$ where the blowby of the cement sheath does not occur according to the target stratum pressure $P_p$, determining the perforation distance $H_K$ to ensure the sealing of the cement sheath according to the annulus pressure $P_A$, and using min ($H_p$, $H_K$), the critical perforation distance that the cement sheath has sufficient strength to prevent blowby and meet the sealing requirements can be determined, which provides data support for the optimization of cement slurry additives and perforation parameter design under complex conditions.

The technical features of the above embodiments can be combined arbitrarily. To make the description concise, all possible combinations of the technical features in the above embodiments are not described. However, as long as there is no contradiction in the combination of these technical features, it should be regarded as the scope of the invention. The above embodiments only express several implementation modes of the invention; the descriptions are more specific and detailed, but should not be interpreted as limiting the scope of the invention. It should be pointed out that for those of ordinary skill in the art, several modifications and improvements can be made without departing from the concept of the invention, which shall all fall within the protection scope of the invention. Therefore, the protection scope of the invention shall be subject to the appended claims.

The invention claimed is:

1. A device for testing strength and sealing performance of cement sheath after perforation, comprising: a cement sheath curing maintenance simulation component, a perforation operation simulation component, and a cement sheath performance test component;
   wherein the cement sheath curing maintenance simulation component comprises:
   a casing (1);
   stratum rocks (8), which are arranged outside the casing (1), and the casing (1) and the stratum rocks (8) enclose a closed annular space; a cement sheath (7) is in cured and maintained in the closed annular space;
   the perforation operation simulation component comprises:
   a perforation gun, and a gun body (29) thereof is provided inside the casing (1); the gun body (29) is provided with a plurality of perforation bullets (30); the plurality of perforation bullets (30) are connected in series via a detonating cord (31) and pass through the top of the casing (1); a gun tail (32) is provided at the bottom of the gun body (29);
   a kill fluid (36), which is tanked between the casing (1) and the gun body (29);
   the cement sheath performance test component comprises:
   a blowby verification booster pump (17); the blowby verification pressure is applied to a lower end surface of the cement sheath (7) through a blowby verification pipeline (15) and a gas-permeable cement isolation ring (14);
   a blowby verification pressure sensor (16), which is provided on the blowby verification pipeline (15);
   a temperature and pressure control system (27), which is electrically connected to the blowby verification pressure sensor (16), and is configured to provide a drawing of the blowby pressure curve under perforation parameters and a perforation distance to test the strength and sealing performance of the cement sheath after perforation; the perforation parameters comprising: aperture, phase, hole density, penetration depth, and explosive payload during the perforation operation, the perforation distance is the the height of the gun tail (32).

2. The device for testing strength and sealing performance of cement sheath after perforation according to claim 1, wherein a casing sealing ring (2) and a lower plug (4) are sequentially provided between the casing (1) and the bottom of the stratum rocks (8) from top to bottom; an upper sealing head (5) and an upper plug (3) are sequentially provided between the casing (1) and the top of the stratum rocks (8) from bottom to top.

3. The device for testing strength and sealing performance of cement sheath after perforation according to claim 2, wherein the cement sheath curing maintenance simulation component further comprises:
   a casing booster pump (20), which is communicated with the casing (1) through a casing pressure pipeline (18);
   a casing internal pressure control valve (19), which is provided on the casing pressure pipeline (18), and the distance from the casing booster pump (20) is less than half of the casing pressure pipeline (18) length.

4. The device for testing strength and sealing performance of cement sheath after perforation according to claim 3, wherein the cement sheath curing maintenance simulation component further comprises:
   a casing heating device (13), which is provided in the casing (1);
   a casing temperature and pressure sensor (6), which is provided in the casing (1) and is electrically connected to the temperature and pressure control system (27).

5. The device for testing strength and sealing performance of cement sheath after perforation according to claim 1, wherein the cement sheath curing maintenance simulation component further comprises:
   a rubber cylinder (9), which is surrounded outside the stratum rocks (8);
   a hydraulic chamber (10), which is surrounded outside the rubber cylinder (9);
   a hydraulic cylinder (11), which is surrounded outside the hydraulic chamber (10);
   a stratum heating jacket (12), which is surrounded outside the hydraulic cylinder (11);
   a confining pressure booster pump (24), which is communicated with the top of the hydraulic chamber (10) through a confining pressure booster pipeline (22);
   a confining pressure sensor (23), which is provided on the confining pressure booster pipeline (22) and is electrically connected to the temperature and pressure control system (27);
   a confining pressure relief valve (26), which is connected to the bottom of the hydraulic chamber (10) through a confining pressure relief pipeline (25).

6. The device for testing strength and sealing performance of cement sheath after perforation according to claim 1, wherein the perforation gun comprises:
   a gun body (29);
   a gun head (28), which is provided at the top of the gun body (29) and is located in the casing (1);
   a gun tail (32), which is provided at the bottom of the gun body (29) and is located in the casing (1);
   a gun body upper plug (33), which is provided outside the casing (1) and located directly above the gun body (29), and is used to guide the detonating cord (31);
   a gun body lower plug (34), which is provided at the bottom of the gun tail (32) and located in the casing (1);
   a gun body handle (35), which is provided at the top of the gun body upper plug (33).

7. The device for testing strength and sealing performance of cement sheath after perforation according to claim 1, wherein the perforation operation simulation component comprises:
   an inner iron sleeve (37), which is surrounded outside the stratum rocks (8);
   an outer iron sleeve (39), which is surrounded outside the inner iron sleeve (37), and concrete (38) is cured between the space enclosed by the inner iron sleeve (37) and the outer iron sleeve (39).

8. A using method of the device for testing strength and sealing performance of cement sheath after perforation according to claim 1, comprising:
   Step 1: according to curing maintenance parameters, a cement sheath (7) is in a process of being cured and the maintained in the closed annular space enclosed by the casing (1) and the stratum rocks (8);
   Step 2: according to perforation operation parameters, perforating with a perforation gun and a detonator equipped with perforation bullets (30) and a detonating cord (31);

Step 3: connecting the blowby verification pressure sensor (16) and the blowby verification booster pump (17) to the blowby verification pipeline (15), selecting an initial pressure $P_0$ to start the blowby verification, and observing blowby pressure curve provided by the temperature and pressure control system (27); if the temperature and pressure within 30 minutes are within the range of $P_0 \times (1 \pm 10\%)$, then selecting the next pressure $P_1$, $P_2$, $P_3$ . . . for blowby verification; monitoring and drawing the relation curve between the blowby pressure curve and time, increasing the pressure until the blowby of the cement sheath (7) occurs, recording the maximum pressure before the blowby occurs as $P_{C0}$, and calculating the blowby velocity $v_0$;

Step 4: taking out the cement sheath, measuring propagation direction of crack and size of crack at different positions from the perforation hole, and drawing the relation curve between the distance of the perforation hole and the crack size;

Step 5: processing cement stone tensile specimens, compressive specimens and permeability test specimens at different positions away from the perforation hole; testing the compressive strength, tensile strength $\sigma_{r0}$ to and permeability $K_0$ of the cement stone after perforation, and drawing the relation curve between the perforation hole distance and the tensile strength $\sigma_{r0}$ to, compressive strength $\sigma_{R0}$ and permeability $K_0$;

Step 6: selecting the next perforation distance $H_1$, $H_1 < H_0$, and measuring the maximum pressure $P_{C1}$ under this perforation distance and the blowby velocity $v_1$, until the designed perforation distances $H_2$, $H_3$ . . . are all tested;

Step 7: drawing the pressure blowby curve at different perforation distances; drawing the relation curves between different perforation distances $H_0$, $H_1$, $H_2$, $H_3$ . . . and the maximum blowby pressure $P_{C0}$, $P_{C1}$, $P_{C2}$, $P_{C3}$ . . ., permeability $K_0$, $K_1$, $K_2$, $K_3$ . . . ;

Step 8: according to the target stratum pressure $P_p$, determining the critical blowby pressure $P_C$ of the cement sheath; when setting the target stratum pressure $P_p$, ensuring that the perforation distance that the blowby of the cement sheath does not occur is greater than or equal to $H_p$;

Step 9: determining the critical permeability $K_C$ of the cement sheath according to annulus pressure $P_A$ control requirements; under the setting of the annulus pressure $P_A$ control requirements, ensuring that the perforation distance of the cement sheath sealing is greater than or equal to $H_K$;

Step 10: selecting the minimum perforation distance ($H_p$, $H_K$) as a critical perforation distance to ensure the strength and sealing performance of the cement sheath.

9. The using method of the device for testing strength and sealing performance of cement sheath after perforation according to claim 8, wherein the curing maintenance parameters in Step 1 comprise:

according to the cementing and perforation operating conditions of the target well, determining the cement slurry system, casing temperature, internal pressure, stratum temperature, confining pressure, temperature and pressure changes during cementing, and cement setting time during the cementing operation.

10. The using method of the device for testing strength and sealing performance of cement sheath after perforation according to claim 8, wherein the perforation operation parameters in Step 2 comprise: aperture, phase, hole density, penetration depth, and explosive payload during the perforation operation.

* * * * *